(12) United States Patent
Kadobayashi et al.

(10) Patent No.: US 9,526,599 B2
(45) Date of Patent: Dec. 27, 2016

(54) OCCLUSAL WEAR EVALUATION APPARATUS AND OCCLUSAL WEAR EVALUATION METHOD

(71) Applicant: KABUSHIKI KAISHA SHOFU, Kyoto (JP)

(72) Inventors: Yusei Kadobayashi, Kyoto (JP); Masako Shigezawa, Kyoto (JP); Keiji Takahashi, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 239 days.

(21) Appl. No.: 14/446,813

(22) Filed: Jul. 30, 2014

(65) Prior Publication Data

US 2014/0343866 A1    Nov. 20, 2014

Related U.S. Application Data

(63) Continuation of application No. 13/589,434, filed on Aug. 20, 2012, now abandoned.

(30) Foreign Application Priority Data

Aug. 23, 2011    (JP) .................................. 2011-181796

(51) Int. Cl.
*A61C 3/00* (2006.01)
*A61C 19/05* (2006.01)
(Continued)

(52) U.S. Cl.
CPC ............... *A61C 19/05* (2013.01); *A61C 11/00* (2013.01); *G06F 19/3437* (2013.01); *A61C 13/0004* (2013.01); *A61C 19/04* (2013.01)

(58) Field of Classification Search
CPC ..... A61C 11/00; A61C 19/05; A61C 13/0004; A61C 19/04; G06F 19/3437
See application file for complete search history.

(56) References Cited

U.S. PATENT DOCUMENTS

| 4,014,097 A | 3/1977 | Pameijer |
| 5,314,332 A | 5/1994 | Lang et al. |

(Continued)

FOREIGN PATENT DOCUMENTS

| JP | 2004-195152 | 7/2004 |
| JP | 2005-193028 | 7/2005 |

(Continued)

OTHER PUBLICATIONS

European Search Report issued Apr. 25, 2013 in corresponding European Patent Application No. 12 18 1285.

(Continued)

*Primary Examiner* — Robert N Wieland
(74) *Attorney, Agent, or Firm* — Wenderoth, Lind & Ponack, L.L.P.

(57) ABSTRACT

An occlusal wear evaluation apparatus capable of quantitatively evaluating an occlusal wear of a used denture reads three dimensional data of the denture before use and three dimensional data of the denture after use. The apparatus calculates a difference in a set value of an articulator allowing a maxillary dental arch and a mandibular dental arch of the denture to occlude between the denture before use and the denture after use, by way of simulating movements of a jaw in the articulator with the three dimensional data of the denture before use and the three dimensional data of the denture after use, and indicates the calculated difference.

10 Claims, 3 Drawing Sheets

(51) Int. Cl.
 *A61C 11/00* (2006.01)
 *G06F 19/00* (2011.01)
 *A61C 13/00* (2006.01)
 *A61C 19/04* (2006.01)

(56) References Cited

U.S. PATENT DOCUMENTS

| | | |
|---|---|---|
| 5,338,198 A | 8/1994 | Wu et al. |
| 5,527,182 A | 6/1996 | Willoughby |
| 2002/0006217 A1 | 1/2002 | Rubbert et al. |
| 2008/0176182 A1 | 7/2008 | Hultgren et al. |
| 2011/0191081 A1* | 8/2011 | Malfliet ............ A61C 11/00 703/11 |

FOREIGN PATENT DOCUMENTS

| | | |
|---|---|---|
| JP | 2005-329055 | 12/2005 |
| JP | 2007-111519 | 5/2007 |
| JP | 2010-17467 | 1/2010 |

OTHER PUBLICATIONS

Ralph DeLong, "Intra-oral restorative materials wear: Rethinking the current approaches: How to measure wear", Dental Materials, vol. 22, pp. 702-711, 2006.

* cited by examiner

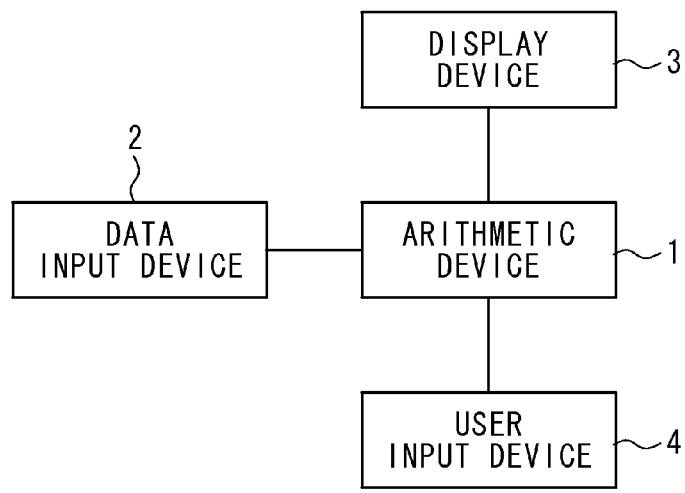
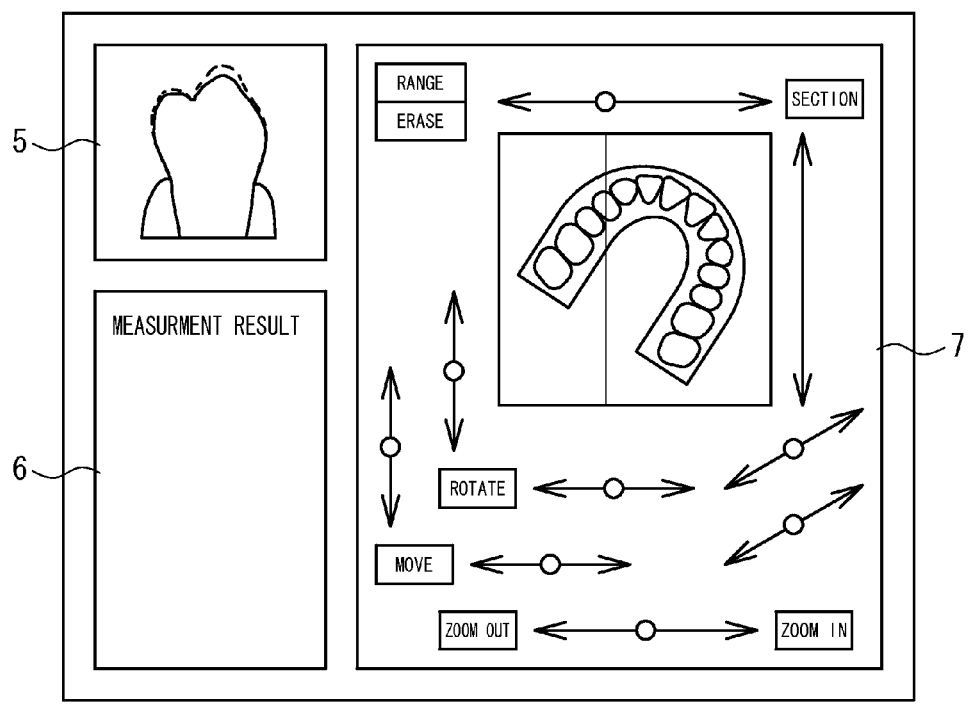

OCCLUSAL WEAR EVALUATION APPARATUS AND OCCLUSAL WEAR EVALUATION METHOD

TECHNICAL FIELD

The present invention relates to an occlusal wear evaluation apparatus and an occlusal wear evaluation method.

BACKGROUND ART

Generally, a denture should be reconfigured periodically. Because a condition in an oral cavity and a muscle force of a patient change over time, an optimum denture for the patient cannot be made by only reconstructing a shape before occlusal wear (abrasion due to dental occlusion) of a presently used denture. Therefore, a dental technician observes a condition of the occlusal wear of the used denture to image an optimum shape of a denture for the patient so as to determine a detailed configuration of a denture to be newly made. For instance, in a case in which the used denture has been unevenly worn, a cusp is adjusted in its shape and position so that a particularly worn part will be hard to wear and the other part will be easy to wear.

When making a denture in such way, a detailed configuration of the denture is determined in a seat of the pants approach by a doctor or a dental technician. Therefore, an apparatus that can evaluate quantitatively an occlusal wear of a used denture is desired in order to allow even a less-experienced doctor or dental technician to determine an optimum denture configuration for a patient.

With respect to a denture configuration, JP 2005-329055 A describes a system scanning three dimensional shape of teeth and indicating the shape of the teeth on a computer, and JP 2004-195152 A describes replicating or simulating an occlusal condition on a computer using three dimensional data of maxillary tooth and mandibular tooth. Also, JP 2007-111519 A describes a system that indicates teeth in a predetermined view and at a predetermined magnification on a screen.

SUMMARY OF THE INVENTION

The object of the present invention is to provide an occlusal wear evaluation apparatus and an occlusal wear evaluation method that can evaluate quantitatively an occlusal wear of a used denture.

In order to achieve the above object, according to the present invention, a first aspect of an occlusal wear evaluation apparatus comprises an input device, an arithmetic device and a display device, wherein the input device is configured to input three dimensional data of a denture before use and three dimensional data of the denture after use into the arithmetic device, the arithmetic device is configured to calculate a set value of an articulator allowing the maxillary dental arch and the mandibular dental arch of the denture to occlude for each of the denture before use and the denture after use by way of simulating movements of a jaw in the articulator with the three dimensional data of the denture before use and the three dimensional data of the denture after use, to calculate a difference in the set value between the denture before use and the denture after use, the set value including at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of sagittal incisal path, and a guidance angle of a lateral incisal path, and the display device is configured to indicate the difference in the set value calculated by the arithmetic device.

According to the present invention, a second aspect of an occlusal wear evaluation apparatus comprises an input device, an arithmetic device and a display device, wherein the input device is configured to input three dimensional data of a plurality of dentures used by a same patient into the arithmetic device, the arithmetic device is configured to calculate a set value of an articulator allowing the maxillary dental arch and the mandibular dental arch of the denture to occlude for the each denture, by way of simulating movements of a jaw in the articulator with the three dimensional data of the dentures, the set value including at least one of a distance between condyle paths, a distance between maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path and a guidance angle of a lateral incisal path, and the display device is configured to indicate the set values calculated by the arithmetic device in a time series chart.

In a denture, because a portion which is heavily used tends to be greatly worn, a lot of jaws incline when an occlusion due to uneven wear occurs. Therefore, in the occlusal wear evaluation apparatus according to the present invention, if a relative angle between the maxillary dental arch and the mandibular dental arch of the denture in a centric occlusal position is calculated, an unevenness of the wear can be quantitatively recognized. Accordingly, a countermeasure such as to reduce unevenness of wear by increasing a contacting area in a mostly used portion can be taken.

In the occlusal wear evaluation apparatus according to the present invention, if a relative position between the maxillary dental arch and the mandibular dental arch of the denture in a centric occlusal position is calculated, variance of an occluding position can be obtained.

In the occlusal wear evaluation apparatus according to the present invention, if at least one of a relative moving distance and a relative moving angle of a sliding movement between the maxillary teeth and the mandibular teeth of the denture from a first occlusal condition to a second occlusal condition is calculated, a variance in a sliding movement of the teeth can be determined.

In the occlusal wear evaluation apparatus according to the present invention, if a volume of the denture is calculated, a total worn amount can be recognized.

In the occlusal wear evaluation apparatus according to the present invention, a height of a cusp which is often used as a reference point may be calculated.

In the occlusal wear evaluation apparatus according to the present invention, a difference in the angles of planes which represent a certain area of the denture may be calculated.

Further, a first aspect of an occlusal wear evaluation method according to the present invention comprises inputting three dimensional data of a denture before use and three dimensional data of the denture after use into a computer, calculating a difference between the denture before use and the denture after use in a set value of an articulator allowing the maxillary dental arch and the mandibular dental arch of the denture to occlude, by way of simulating movements of a jaw in the articulator with the three dimensional data of the denture before use and the three dimensional data of the denture after use on the computer, the set value including at least one of a distance between condyle paths, a distance between maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path and a guidance angle of a lateral incisal path which are set values, and indicating the calculated difference on a screen.

Further, a second aspect of an occlusal wear evaluation method according to the present invention comprises inputting three dimensional data of a plurality of dentures used by the same patient into a computer, calculating a set value of an articulator allowing the maxillary dental arch and the mandibular dental arch of the denture to occlude for each denture by way of simulating movements of a jaw in the articulator with the three dimensional data of the dentures on the computer, the set value including at least one of a distance between condyle paths, a distance between maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path and a guidance angle of a lateral incisal path, and indicating the calculated set values in a time series chart on a screen.

According to the present invention, a wear of a denture due to use is quantified to be indicated, and therefore a correct diagnosis and a redesign of a denture can be made.

BRIEF DESCRIPTION OF THE DRAWINGS

FIG. 1 is a schematic configuration diagram of an occlusal wear evaluation apparatus as an embodiment of the present invention;

FIG. 2 shows an example of a screen indication of the occlusal wear evaluation apparatus in FIG. 1;

DETAILED DESCRIPTION OF THE PREFERRED EMBODIMENT

Figure 3:
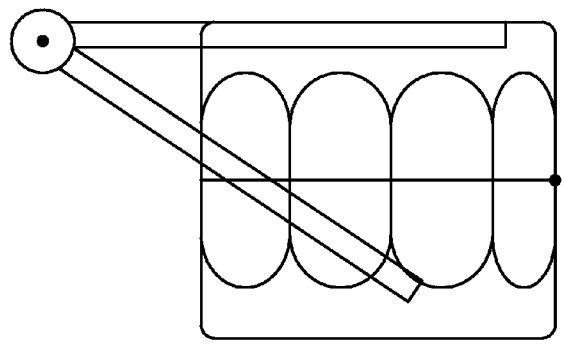
FIG. 3 is a schematic view of a denture before use evaluated on the occlusal wear evaluation apparatus in FIG. 1.

Hereinafter, an embodiment of the present invention is described with reference to the drawings. An occlusal wear evaluation apparatus according to the present invention can be realized using a computer system that comprises an arithmetic device 1, a data input device 2, a display device 3 and a user input device 4 as shown in FIG. 1.

The arithmetic device 1 can be substantialized using a personal computer and a software program, while the arithmetic device 1 may be exclusively designed. The data input device 2 does not need to be only an apparatus such as a three dimensional scanner reading directory three dimensional shape, but can also be a device for inputting three dimensional data which is read by an external three dimensional scanner and the like into the arithmetic device 1, such as a media reading device, for instance, a memory device or a disc drive, or a data communication device. The display device 3 may be a common display. As the user input device 4, a generalized input device such as a keyboard and a mouse can be used.

The occlusal wear evaluation apparatus according to the present invention uses the data input device 2 to input three dimensional data of a denture before use and three dimensional data of the same denture which has been used by a patient and worn, into the arithmetic device 1, and calculates variations in various physical quantities of the denture between before and after use so as to indicate on the display device 3.

FIG. 2 shows an example of a screen indication of the display device 3. In this example, a sectional display portion 5 for indicating a sectional view of the denture is arranged in an upper left part of the screen, a result display portion 6 for indicating differences in physical quantities of the denture before and after use is arranged in a lower left part of the screen, and a general display portion 7 for indicating the entire denture schematically and specifying a position of a cross section indicated in the sectional display portion 5 is arranged in a right part of the screen.

The sectional display portion 5 indicates a sectional shape of the denture after use and a sectional shape of the same denture before use at the same position in an overlaid manner with different line types and/or colors. As an example, in FIG. 2, a sectional shape of a denture after use is indicated by solid lines, and an outline of a cross section of the same denture before use sectioned at the same position is indicated by dashed lines. Thereby, a wear of the denture in a certain cross section is visualized in an understandable manner.

The result display portion 6 indicates a difference in physical quantities between a denture before use and the denture after use (variations due to an occlusal wear). The differences in physical quantities calculated by the arithmetic device 1 and indicated in the result display portion 6 include a variation in a relative angle between a maxillary dental arch and a mandibular dental arch, a variation in a relative position between a specific reference point of a maxillary dental arch and a specific reference point of a mandibular dental arch (such as an occlusal vertical dimension).

The physical quantities indicated in the result display portion 6 include a relative moving distance and a relative moving angle in a sliding movement between maxillary teeth and mandibular teeth from a first occlusal condition (for instance, a centric occlusal position) to a second occlusal condition (for instance, a lateral occlusal position), a volume of a denture and a height of a cusp. The differences in physical quantities indicated in the result display portion 6 may further include an angular difference (a variation in a direction of a normal line) of planes which represent a certain area of the denture, for instance, planes approximated by the method of least squares, and the like.

Further, the variations indicated in the result display portion 6 may include differences between before and after use in physical quantities (for instance, sectional area and height) in the cross section indicated on the sectional display portion 5.

Further, the occlusal wear evaluation apparatus preferably simulates movements of a jaw in an articulator by the arithmetic device 1 so that variations in set values (for instance, a distance between condyle paths, a distance between maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path and a guidance angle of a lateral incisal path) in the articulator can be calculated to be indicated on the result display portion 6.

The general display portion 7 is mainly intended to be utilized by a user to determine a cross-sectional position to be indicated on the sectional display portion 5, through the user input device 4. Therefore, the general display portion 7 is to show dental arches schematically, and is not required to show any specific shape based on actual data. The display on the sectional display portion 5 preferably is successively renewed together with a relocation of the cross-sectional position determined in the general display portion 7. While it is also idealistic that the indication in the result display portion 6 is successively renewed together with a relocation of the cross-sectional position, the indication in the result display portion 6 may be renewed at a timing designated by a user via the user input device 4, so as to reduce an arithmetic load for the arithmetic device 1.

The general display portion 7 indicates bar handles for moving cursors on the screen using the user input device 4 so as to move and rotate the displayed dental arches in respective directions of x, y, z, bar handles to designate a cross-sectional position to be displayed in the sectional display portion 5 on the dental arches displayed in the general display portion 7, and a bar handle for zooming the display in the sectional display portion 5.

Further, the general display portion 7 preferably specifies a position in which a difference of a physical quantity as indicated in the result display portion 6 is maximized and is able to indicate the position on the screen. For instance, a position of a cusp which has most greatly varied in position, a tooth which has most greatly changed in volume and others may be specified in a manner of changing color, indicating a marker or the like.

Figure 4:
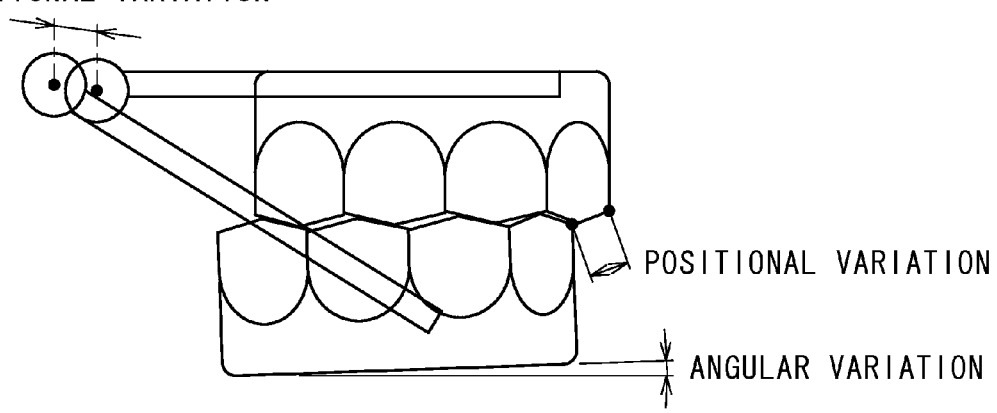
FIG. 4 is a schematic view of a denture after use evaluated on the occlusal wear evaluation apparatus in FIG. 1.

FIG. 3 schematically shows a denture before use and FIG. 4 schematically shows the denture after use, in order to describe how to utilize the occlusal wear evaluation apparatus according to the present invention. The occlusal wear evaluation apparatus occludes the three dimensional data of the maxillary teeth and three dimensional data of the mandibular teeth, respectively, for the denture before use and the denture after use so as to replicate respective centric occlusal positions where contacting points are maximized. Then, a difference between a relative angle of the mandibular dental arch with respect to the maxillary dental arch of the denture before use and a relative angle of the mandibular dental arch with respect to the maxillary dental arch of the denture after use is calculated, as three angles in axial directions of x, y, z, to be indicated in the result display portion 6. For instance, x is a direction connecting both condyles, y is a direction perpendicular to the x axis and parallel to the occlusal plane, and z is a direction perpendicular to x and y.

Further, the occlusal wear evaluation apparatus according to the present invention calculates relative positions of the mandibular dental arch with respect to the maxillary dental arch between the denture before use and the denture after use in three distances in axial directions of x, y, z, and indicates the distances in the result display portion 6. This change in relative positions preferably is calculated in a manner assuming that three points as center points of both condyle paths and a center point between both cutting edges of central incisors are reference points.

To this end, the occlusal wear evaluation apparatus specifies positions of articular fossae with respect to the maxillary teeth and positions of condyles with respect to the mandibular teeth for the three dimensional data of the denture before use. In this case, the articular fossae and the condyles in the denture before use are determined so that the articular fossae and the condyles respectively coincide with each other in the centric occlusal position. For the denture after use, positions of articular fossae and positions of condyles are calculated assuming that the relative position between the maxillary teeth and the articular fossae and the relative position between condyles and the mandibular teeth specified for the denture before use do not change.

Notably, the positions of the reference points on the maxillary teeth and the positions of the reference points on the mandibular teeth coincide in FIG. 3, and therefore relative positions between the reference points on the maxillary teeth and the reference points are equal to the variations between FIG. 3 and FIG. 4.

A denture in which the relative angle between the maxilla and the mandible does not vary due to an occlusal wear is considered as being in an ideal condition where abrasions are even without an uneven wear. Also, a change in a position of the condyle of the denture with respect to the articular fossa due to an occlusal wear is considered as suggesting a possibility of a temporomandibular arthrosis. Therefore, these figures give great indications to evaluate whether or not the denture is adapted to the patient.

Also, a change in height of a cusp of each tooth gives an indication to make a diagnosis of an occlusion. Specifically, variations of heights of a buccal cusp of a mandibular first molar and a mesiolingual cusp of a maxillary first molar give indications of a variation in an occlusal vertical dimension.

Further, the occlusal wear evaluation apparatus can determine and indicate a portion with a large variation between before and after use, i.e., a largely worn portion, so as to notify a doctor or a technician of a position to be especially attended. In a case where a volume of the denture is significantly reduced, a crunching (unintentional biting) is suspected.

Figure 5:
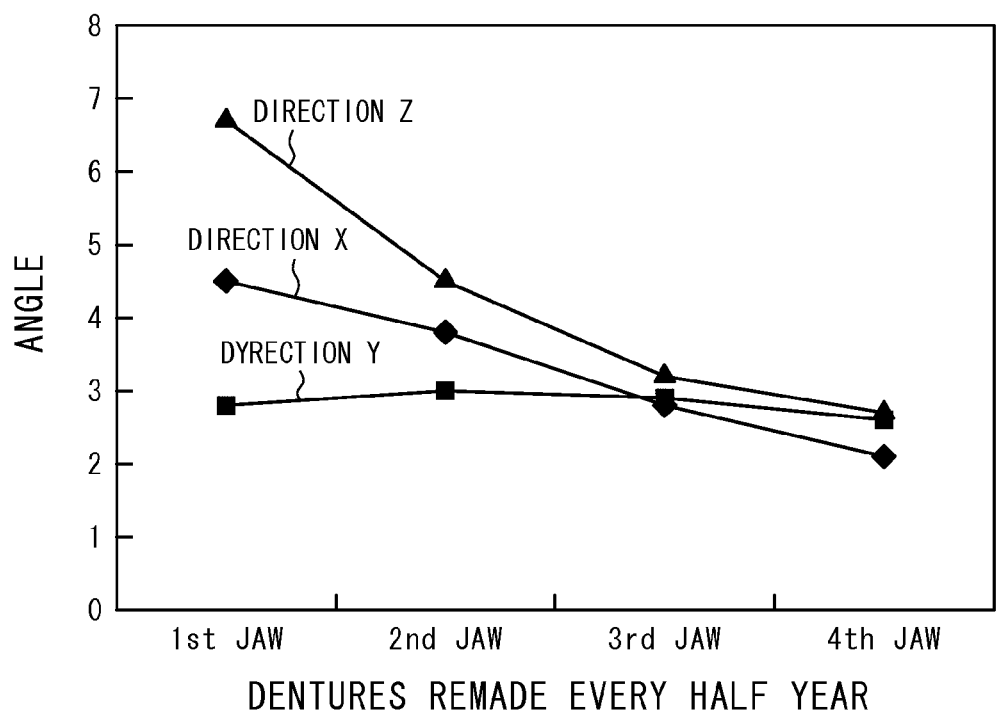
FIG. 5 is an example of a chart indicated on the occlusal wear evaluation apparatus in FIG. 1.

Further, the occlusal wear evaluation apparatus according to the present invention preferably can indicate differences in a physical quantity between before and after use in comparison among plural dentures. FIG. 5 shows a chart of variations in a relative angle between maxillary dental arches and mandibular dental arches due to wear of the respective dentures which are remade for the same patient every half year. In this example, the variation in the relative angle gets smaller gradually, and therefore it can be confirmed that the newer denture is better adapted to the patient.

A variation in a relative angle between a maxillary dental arch and a mandibular dental arch due to occlusal wear can be caused by an alteration of a configuration of a denture as well as by a variation in masticatory ability due to a change in muscle strength or other reasons. Therefore, this information does not lead to an absolute conclusion directly, but is beneficial information which contributes to making an integrated diagnosis by a doctor with an interview result and the like in mind.

REFERENCE SIGN LIST

1 . . . arithmetic device
2 . . . data input device
3 . . . display device
4 . . . user input device
5 . . . general display portion
6 . . . result display portion
7 . . . sectional display portion

What is claimed is:
1. A denture occlusal wear evaluation method for evaluating a denture by a comparison between the denture before being used by a person and the denture after being used by the person, said wear evaluation method comprising:
   first receiving three dimensional data of the denture before use;

first simulating movements of a jaw in an articulator with the three dimensional data of the denture before use so that a first set of values in the articulator are calculated, wherein the first set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

second receiving three dimensional data of the denture after use;

second simulating movements of a jaw in an articulator with the three dimensional data of the denture after use so that a second set of values in the articulator are calculated, wherein the second set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

calculating differences between the first set of values and the second set of values; and displaying the calculated differences, wherein each of said first simulating and said second simulating includes calculating a volume of the denture, and wherein the displaying includes indicating the volume calculated by said calculating.

2. A denture occlusal wear evaluation method for evaluating a denture by a comparison between the denture before being used by a person and the denture after being used by the person, said wear evaluation method comprising:

first receiving three dimensional data of the denture before use;

first simulating movements of a jaw in an articulator with the three dimensional data of the denture before use so that a first set of values in the articulator are calculated, wherein the first set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

second receiving three dimensional data of the denture after use;

second simulating movements of a jaw in an articulator with the three dimensional data of the denture after use so that a second set of values in the articulator are calculated, wherein the second set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

calculating differences between the first set of values and the second set of values; and displaying the calculated differences, wherein each of said first simulating and said second simulating includes calculating a height of a cusp of the denture, and wherein said displaying includes indicating the height of the cusp calculated by said calculating.

3. A denture occlusal wear evaluation method for evaluating a denture by a comparison between the denture before being used by a person and the denture after being used by the person, said wear evaluation method comprising:

first receiving three dimensional data of the denture before use;

first simulating movements of a jaw in an articulator with the three dimensional data of the denture before use so that a first set of values in the articulator are calculated, wherein the first set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

second receiving three dimensional data of the denture after use;

second simulating movements of a jaw in an articulator with the three dimensional data of the denture after use so that a second set of values in the articulator are calculated, wherein the second set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

calculating differences between the first set of values and the second set of values; and displaying the calculated differences, wherein each of said first simulating and said second simulating includes calculating an angular difference of planes which represent a certain area of the denture, and wherein said displaying includes indicating the angular difference calculated by said calculating.

4. A denture occlusal wear evaluation method for evaluating a first denture and a second denture which are both used by the same person, said wear evaluation method comprising:

first receiving three dimensional data of the first denture after use by the person;

first simulating movements of a jaw in an articulator with the three dimensional data of the first denture after use so that a first set of values in the articulator are calculated, wherein the first set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

second receiving three dimensional data of the second denture after use by the person;

second simulating movements of a jaw in an articulator with the three dimensional data of the second denture after use so that a second set of values in the articulator are calculated, wherein the second set of values includes at least one of a distance between condyle paths, a distance between a maxillary dental arch and a mandibular dental arch, an inclination of a sagittal condylar path, an angle of a balancing side lateral condylar path, an amount of an immediate side shift, an angle of a working side lateral condylar path, an inclination of a sagittal incisal path, and a guidance angle of a lateral incisal path;

calculating differences between the first set of values and the second set of values; and displaying the calculated differences.

5. The denture occlusal wear evaluation method according to claim 4, wherein each of said first simulating and said second simulating includes calculating a relative angle between the maxillary dental arch and the mandibular dental arch of the denture in a centric occlusal position, and wherein said displaying includes indicating the relative angle calculated by said calculating.

6. The denture occlusal wear evaluation method according to claim 4, wherein each of said first simulating and said second simulating includes calculating a relative position between the maxillary dental arch and the mandibular dental arch of the denture in a centric occlusal position, and wherein said displaying includes indicating the relative position calculated by said calculating.

7. The denture occlusal wear evaluation method according to claim 4, wherein each of said first simulating and said second simulating includes calculating at least one of a relative moving distance and a relative moving angle of a sliding movement of maxillary teeth and mandibular teeth of the denture from a first occlusal condition to a second occlusal condition, and wherein said displaying includes indicating the at least one of the relative moving distance and the relative moving angle calculated by said calculating.

8. The denture occlusal wear evaluation method according to claim 4, wherein each of said first simulating and said second simulating includes calculating a volume of the denture, and wherein said displaying includes indicating the volume calculated by said calculating.

9. The denture occlusal wear evaluation method according to claim 4, wherein each of said first simulating and said second simulating includes calculating a height of a cusp of the denture, and wherein said displaying includes indicating the height of the cusp calculated by said calculating.

10. The denture occlusal wear evaluation method according to claim 4, wherein each of said first simulating and said second simulating includes calculating an angular difference of planes which represent a certain area of the denture, and wherein said displaying includes indicating the angular difference calculated by said calculating.

* * * * *